United States Patent [19]

Kanou et al.

[11] Patent Number: 4,675,289

[45] Date of Patent: Jun. 23, 1987

[54] METHOD OF MEASURING THE NUMBER OF EUMYCETE CELLS

[75] Inventors: Hideo Kanou, Yokosuka; Masahiro Kamata; Shigeru Yamanaka, both of Yokohama, all of Japan

[73] Assignee: Ajinomoto Company, Incorporated, Tokyo, Japan

[21] Appl. No.: 599,632

[22] Filed: Apr. 12, 1984

[30] Foreign Application Priority Data

Apr. 12, 1983 [JP] Japan ................... 58-64308

[51] Int. Cl.$^4$ .............................................. C12Q 1/34
[52] U.S. Cl. ....................................... 435/18; 435/34; 435/39; 435/911
[58] Field of Search ............................ 435/18, 34, 39

[56] References Cited

U.S. PATENT DOCUMENTS 3,451,893  6/1969  Sanders ................................. 435/34

FOREIGN PATENT DOCUMENTS 0000063  12/1978  European Pat. Off. .
6064797   6/1981   Japan .
1547747   6/1979   United Kingdom .

OTHER PUBLICATIONS

Godsey et al. Journal of Clinical Microbiology (1981), vol. 13, No. 3, pp. 483–490.
Derwent Publication 00141, Nov. 18, 1982.
Manual of Clinical Microbiology Chapter 55, 3rd Edition Lennett et al. (1980) page 566.

Primary Examiner—Sam Rosen
Assistant Examiner—William J. Herald
Attorney, Agent, or Firm—Oblon, Fisher, Spivak, McClelland & Maier

[57] ABSTRACT

A method of measuring the number of eumycete cells in a sample which comprises preparing a solution or suspension containing a sample of a medicine, food, drink, cosmetic or water, adding to said solution or suspension a 7-amino-4-methyl-coumarin derivative represented by formula (1):

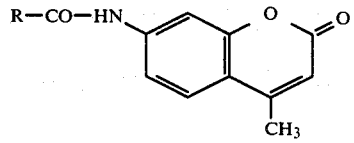

wherein R is an alkyl group, an allyl group, an aralkyl group, or a heterocyclic group, or R—CO— is an amino acid or peptide residue, said derivative not inhibiting the hydrolysis of the amide bond of formula (1) by microorganism hydrolases contained in the samples; and measuring the fluorescence of 7-amino-4-methyl-courmarin released by the microorganism hydrolases.

11 Claims, 2 Drawing Figures

METHOD OF MEASURING THE NUMBER OF EUMYCETE CELLS

BACKGROUND OF THE INVENTION

1. Field of the Invention:

This invention relates to a method of measuring the number of cells of microorganisms being present in food, medicines, cosmetics and water.

2. Description of the prior Art:

In the production and quality control of food, medicines, cosmetics and so on, the number of cells of small amounts of microorganisms contained in these samples must be measured in a short time. Moreover, a wide variety of microorganisms must be detected in a short time since the kinds of microorganisms incorporated into these samples cannot initially be known. For measuring the number of cells of microorganisms in a short time, there is mentioned a well-known method comprising hydrolyzing a 4-methylumbelliferone derivative (abbreviated as 4MU-derivtive hereinafter) with the enzymes of microorganisms contained in samples and determining the resulting 4-methyl-umbelliferone (abbreviated as 4MU nereinafter) with a fluorophotometer (Japanese Patent Laid-Open No. 144995/1982). This method is advantageous because the number of cells of small amounts of microorganisms can be measured in a short time. However, this method had a drawback that all the microorganisms contained in samples such as food cannot always be detected.

SUMMARY OF THE INVENTION

The inventors of this application have found that the number of cells of a wide variety of microorganisms contained in food and so on in small quantities can be measured with very high sensitivity in a short time when using 7-amino-4-methyl-coumarin derivatives (abbreviated as AMC-derivative hereinafter) instead of 4MU-derivative. This invention consists of two methods, method A and method B.

Method A comprises the following processes. Namely, method A is to provide a method of measuring the number of cells of microorganisms, which comprises proces (1) preparing different concentrations of solutions or suspensions containing some samples selected for test, process (2) keeping said solutions or suspensions at a temperature from 20° C. to 70° C., process (3) adding AMC-derivatives to said solutions or suspensions after process (1) and before or after process (2), and process (4) determining 7-amino-4-methyl-coumarin produced in said solutions or suspensions after processes (2) and (3).

Method B is to provide a method of measuring the number of cells of microorganisms, which comprises adding AMC-derivatives to certain amounts of samples to be tested, keeping the mixtures at a temperature from 20° C. to 70° C., and determining the resulting 7-amino-4-methyl-coumarin.

Either method A or B may suitably be selected when microorganisms contained in samples such as food are measured. In general, method A is used for measuring quite small amounts of microorganisms contained in sampies such as food (for example, when the number of cells of microorganisms is less than $10^4$ per 1 g or 1 ml of a sample). On the contrary, method B is selected when the number of cells of microorganisms contained in a sample such as food is more than $10^4$ per 1 g or 1 ml of the sample.

It is to be noted that even when the number of cells is more than 104 per 1 g or 1 ml, method A is desirable for the precise measurement.

Samples to be used for the measurement of the cell number include both solid and liquid materials such as food and drink, medicines, cosmetics, and water. Food and drink include solid materials such as solid seasonings and dry food, something containing vegetables and meat such as vegetable salads, aqueous pasty seasonings, raw fishes and shellfishes such as sashimi, and meat products such as ham and live-stock meat. Samples containing solids are homogenized by grinding the solids to fine particles with a whirling blender or a mixer to the extent that microorganisms in the samples are nor killed, and then can be handled in the same manner as liquid ones.

The marks •, ○, □ and △ are used to indicate the relation between the fluorescence strength and the number of cells of microorganisms contained in 10 ml of each of the water taken from the Tama River, water waste in food-producing steps, city sewage, and domestic water waste, respectively.

Figure 2:
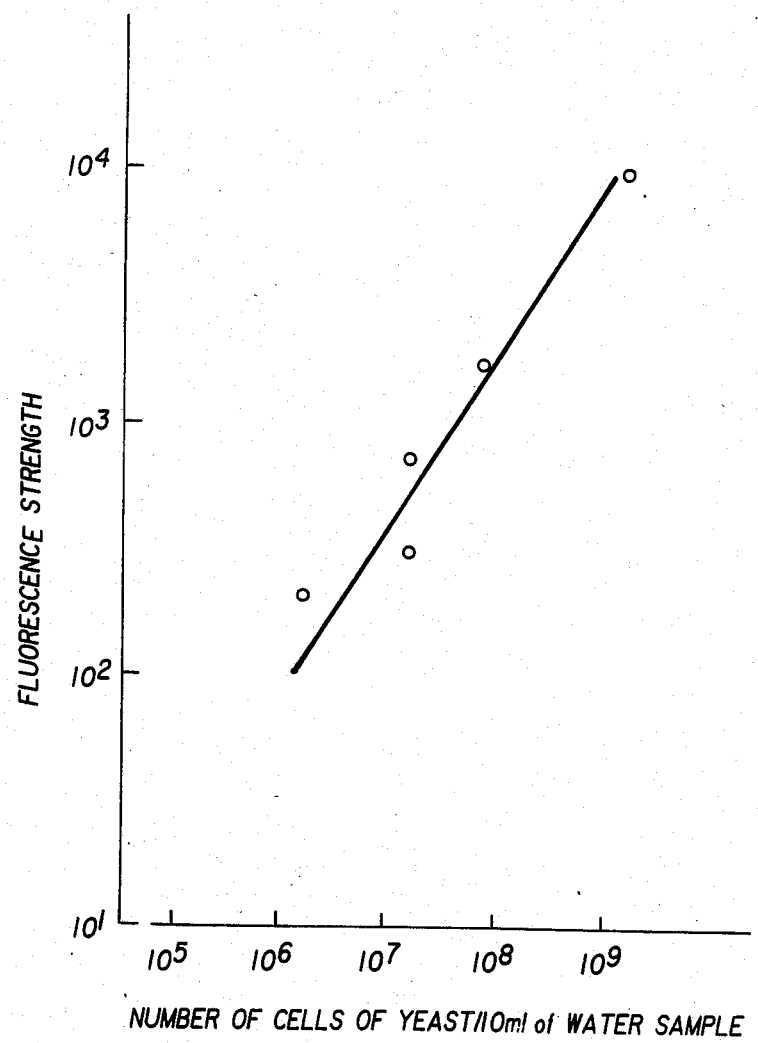

FIG. 2 shows the relation between the fluorescence strength and the number of cells of yeast contained in 10 ml of each water sample.

DETAILED DESCRIPTION OF THE PREFERRED EMBODIMENTS

The following is the explanation as to the processes of method A of this invention.

Process (1) provides an operation of preparing different concentrations of solutions or suspensions of samples. In this case, solutions containing nutrients needed for the growth of microorganisms are used for dilution. Any dilution will do if a constant dilution is repeated, and so one or several test tubes having the same dilution are used. Usually, one-tenth dilution is repeated several times to prepare three to five test tubes having the same dilution.

Process (2) is carried out after process (1). Said solutions or suspensions are kept at a temperature from 20° C. to 70° C. for a certain period of time. In this process, one or more microorganisms when contained in said solutions or suspensions are grown by keeping the temperature at 20° C.–70° C. for a certain period of time.

In order to measure particularly coliforms among microorganisms contained in samples, a substance to selectively grow coliforms such as desoxycholic acid may be added to the diluted solutions used in process (1) in a typical concentration. In order to measure only Eumycetes, antibiotics such as chloramphenicol and penicillin which innibit the growth of bacteria and do not prevent that of Eumycetes may be added to the diluted solutions used in process (1) in a typical concentration. In order to measure Thermotolerants, samples may be treated with heat under ordinary conditions wherein Thermotolerants are not killed and Mesophiles are killed, after the homogenization of the samples prior to process (1). In order to measure only anaerobes, process (2) may be conducted under the anaerobic conditions of said solutions or suspensions. In order to measure aerobes, said solutions or suspensions are kept warm with shaking. It is desirble to keep warm said solutions or suspensions at the most suitable temperature for growing microorganisms to be measured. The temperature suitable for measuring the numbers of microorganism celis belonging to Mesophile ranges from 20° C. to 40° C., and that for Thermophile from 40° C. to 70° C.

In order to measure bacteria present among the microorganisms contained in samples, said solutions or suspensions are kept warm for a period of time ranging from 30 minutes to 8 hours. Even in the case of Eumycetes such as mold and yeast which grow very slowly in 5 or more days until the growth is visually observable, said solutions or suspensions are kept warm only for 48 hours at the longest.

In order to measure only the specific microorganism in samples as stated above, process (2) should be carried out under the conditions for growing only the specific one.

In process (3), one or more AMC-derivatives are added to said solutions or suspensions immediately after process (1) or after the completion of process (2).

AMC-derivatives are represented by general formula (1)

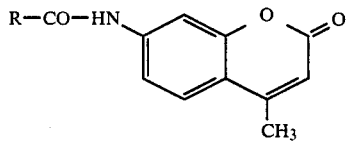

wherein R—CO— indicates amino acid or peptide residues, or where R— represents an alkyl group and does not inhibit the hydrolysis caused by the hydrolase of microorganisms contained in said solutions and suspensions.

Preferred alkyl groups include hydrocarbons conraining 1 to 20 carbon atoms, which may optionally be substituted by one or more organic functional groups selected from the group consisting of amino, hydroxy, chloro, bromo, fluoro, trifluoromethyl, carboxy, carboxymethyl, or phenyl. Of these, alkyl groups which are unsubstituted or which have no more than two of the names substituents are preferred. Alkyl groups of the invention may be saturated or unsaturated, cyclic or acyclic.

preferred are alkyl groups with no more than one unsaturation or ring. More preferred are alkyl groups which otherwise have the same limitations but which have 1 to 5 carbons.

Most preferred for R are groups formed from naturally occurring amino acids or peptides composed of naturally occurring amino acids having the general formula $RCO_2H$. The peptides or amino acids may optionally contain substitution on the terminal nitrogen by groups known to be protective groups for amines during synthetic reactions including t-butyloxy-carbonyl, (Boc); benzyl-oxy-carbonyi, (Z); or fluorenyl-methoxy-carbonyl, (Fmoc).

R may also be a 5 or 6-membered heterocyclic ring containing 1 or 2 heteroatoms including O, S or N. The heterocyclic ring may be saturated, unsaturated or aromatic.

Moreover, one or more 4MU-derivatives can be added besides AMC-derivatives. These 4MU-derivatives are represented by general formula (2)

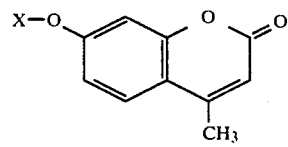

X—O— indicates a sugar radical, an alcohol radical or a phosphate radical, and does not inhibit the hydrolysis caused by the hydrolase of microorganisms contained in said solutions or suspensions. By radical is meant an —OH containing molecule which is missing the hydrogen normally bonded to the oxygen in said molecule.

Said derivatives can be added to the maximum amount soluble in said solutions or suspensions, but in this invention, $10^{-4}M$ is usually added.

In order to enhance the hydrolase activity of microorganisms, activators can be added to increase the yields of AMC and 4MU in said solutions or suspensions. As activators, there are mentioned, for example, cobalt ion when using aminopeptidase as the hydrolase and magnesium ion when using phosphatase.

When process (3) is conducted after process (1), followed by process (2), process (4) should immediately be carried out. On the contrary, when process (3) is conducted after processes (1) and (2) said solutions or suspensions are kept warm at a temperature from 20° C. to 70° C. usually for a further period of time ranging from 30 minutes to 1 hour after process (3).

In this case, after process (2) and before process (3), said solutions or suspensions are centrifuged, and the resulting precipitate parts can be used for achieving process (3). The addition of such centrifugation process brings about the increase of the microorganism concentrations because the microorganisms contained in said solutions or suspensions are collected in the precipitate parts. Further, this centrifugation process can be followed by the addition to organic solvents such as toluene, physical destruction such as ultrasonic wave treatment and French press, and enzymatic destruction caused by, for example, lysozyme, all of which are known as processes for destroying the cells of microorganisms.

Process (4) is conducted after completing processes (1) to (3), wherein AMC or 4MU produced in said solutions or suspensions is detected with a fluorophotometer. This process is only for detecting qualitatively whether AMC or 4MU is produced in said solutions or suspensions.

The numbers of cells of microorganisms contained in samples can be obtained from the maximum dilution of said solutions or suspensions wherein fluorescence is detected by process (4). One example is given below to explain the manner of measuring the number of cells. A sample is diluted to one-tenth concentration in several continuous dilurion steps to obtain five test tubes of solutions or suspensions in each dilution step, which are examined to detect fluorescence according to method (A) so as to find how many of the five in each dilution step have detectable fluorescence. On the basis of these findings, the numbers of cells of microorganisms in the samples are calculated by the Most probabie Number table (Notification No. 59 of Environmental Agency, Dec. 28, 1971).

This MPN method can count the numbers of cells of small amounts of microorganisms more precisely than the Agar plate Counts method.

The following is an explanation as to the method (B) of this invention. Method (B) comprises the same processes as achieved in method (A) except for excluding process (2) and including another step of quantitatively determining fluorescence strength in process (4). This method is to provide the measurement of the numbers of cells of microorganisms contained in samples on the ground that the number of cells is correlative with the fluorescence strength. In method (B), the diluted solutions in the process corresponding to process (1) of mernod (A) do not have to contain nutrients needed for the growth of microorganisms. This dilution process of samples may be followed by the addition of organic solvents such as toluene, physical destruction such as ultrasonic wave treatment and French press, and enzymatic destruction caused by, for example, lysozyme, which are known as processes for destroying the cells of microorganisms. Next, the process correponding to process (3) of method (A) is conducted. In this regard, the temperature for keeping warm ranges from 20° C. to 70° C., and the period of time from 30 minutes to 2 hours. After this process of keeping warm, the quantities of fluorescence of AMC or 4MU produced in said solutions or suspensions are determined.

On the basis of the correlation between the previously obtained number of cells of microorganisms and quantities of fluorescence, any number of cells of microorganisms contained in samples can be calculated from the quantities of fluorescence of said solutions or suspensions. Method (B) cannot be used when 104 or less cells are contained in 1 g or 1 ml of a sample. Also, method (B) is inferior to method (A) as to precision in the measurement of cells, but has the merit of conducting the measurement in a very short time because of excluding process (2) of method (A).

As described above, the methods of this invention are to provide the exact measurement of the cells of small amounts of various microorganisms contained in samples in a short time.

This invention is explained further in detail by the following Examples.

EXAMPLE 1

Each of the strains shown in Table 1 was incubated in a culture solution medium of pH 6.5 containing 0.5% peptone and 0.1% yeast extract with shaking for 48 hours, and each of the cultured cells was inoculated in a test tube containing 9 ml of the solution medium of the same composition as above after dilution so that $10^2$–$10^3$ cells can be inoculated in each tube. Then the cells of bacteria were grown at 35° C. for 24 hours, and those of Eumycetes at 30° C. for 72 hours. After completing the cultivation, said culture solution was minutes 100 times with 0.9% brine. Then, 1 ml of the thus diluted solution was added to 2 ml of each solution prepared by dissolving separately each of $10^{-4}$M of L-arginyl-7-amino-4-methyl-coumarin (abbreviated as AMC-Arg hereinafter), L-leucyl-7-amino-4-methyl coumarin (abbreviated as AMC-Leu hereinafter), 4MU-glucose, and 4MU-phosphoric acid (abbreviated a 4MU-P hereinafter) in 0.05 M barbital buffer of pH 7.5 containing $10^{-3}$M of magnesium chloride, and the mixed solutions were kept warm at 40° C. for 1 hour. After the completion of keeping warm, 0.1 M glycine buffer of pH 11.0 was added, and then the fluorescence strength was determed with a fluorophotometer (RF-520 type made by Shimadzu Seisakusho Ltd., using 30 micro flow cell) under the conditions of an excitation wavelength of 360 nm and a fluorescence wavelength of 450 nm. The results were given in Table 1.

TABLE 1

| | | AMC-derivative or 4MU-derivative | | | |
| | | AMC derivative | | 4MU derivative | |
| Strains | | AMC—Arg | AMC—Leu | 4MU—P | 4MU—glucose |
|---|---|---|---|---|---|
| (Bacteria) | | | | | |
| Micrococcus luteus | ATCC 1003 | +++ | +++ | + | − |
| Streptococcus agalactiae | ATCC 13833 | +++ | ++ | − | − |
| Lactobacillus delbrueckii | ATCC 9649 | +++ | ++ | − | − |
| Bacillus brevis | ATCC 8185 | ++ | ++ | + | + |
| Bacillus stearothermophilus | ATu 12980 | +++ | ++ | + | + |
| Streptomyces albus | ATCC 3004 | ++ | ++ | − | − |
| Alcaligenes faecalis | ATCC 25094 | +++ | +++ | − | − |
| Acinetobacter curcoaceticus | ATCC 23035 | +++ | +++ | + | − |
| Proteus morganii | IFO 3848 | ++ | ++ | + | − |
| Enterobacter aerogenes | ATCC 13048 | +++ | ++ | + | − |
| Citrobacter freundii | ATCC 10787 | +++ | ++ | + | − |
| Pseudomonas aeruginosa | ATCC 27853 | +++ | +++ | + | − |
| Pseudomonas fluorescens | ATCC 13525 | +++ | ++ | + | − |
| Pseudomonas caliophili | ATCC 25418 | +++ | +++ | + | − |
| Aeromonas hydrophila | NRRLB-909 | +++ | ++ | + | − |
| Chromobacterium violaceum | ATCC 12472 | ++ | +++ | − | − |
| Flavobacterium halmephilum | ATCC 1917 | +++ | ++ | + | − |
| (Eumycetes) | | | | | |
| Mucor rouxii | ATCC 24905 | + | +++ | − | − |
| Aspergillus flavus | ATCC 15517 | ++ | ++ | − | − |
| Penicillium citreo-viride | ATCC 10425 | ++ | ++ | − | − |
| Alternaria alternata | ATCC 13963 | +++ | ++ | − | + |
| Pichia membranaefaciens | IFO 460 | +++ | ++ | − | − |
| Torulopsis coliculosa | IFO 1083 | +++ | +++ | − | − |
| Geotrichum candidum | ATCC 4798 | + | +++ | + | − |

The signs shown in Table 1 have the following meanings:
−: fluorescence strength 10 or less
+: fluorescence strength 10–100
++: fluorescence strength 100–1000
+++: fluorescence strength 1000 or more As shown in Table 1, it was found that fluorescence was produced in higher yields and by a larger variety of microorganisms when using AMC-derivatives than 4MU-derivatives.

EXAMPLE 2

Three samples of 10 ml of each of water obtained from the Tama River, domestic water waste, water waste discharged in food-producing steps, and city sewage were collected. These warer samples were centrifuged at 3,500 rpm for 10 minutes (using a H-107 type centrifuge made by Kekusan Centrifuge Co., Ltd.). To each of the resulting precipitate parts was added 2.5 ml of 0.02 M barbital buffer of pH 7.0 containing $10^{-4}$M of AMC-Leu and $10^{-3}$M of magnesium chloride. The mixtures were treated with a micro ultrasonic wave cell grinder (Sonicator W-10 type made by Wakenyaku Co., Ltd.) at 50w for 3 minutes. After treatment, these reaction solutions were maintained at 37° C. for 60 minutes. Then, 1 ml of 0.1 M glycine buffer of pH 11.0 was added to each of the reaction solutions, and the mixtures were centrifuged at 3000 rpm for 5 minutes. The resulting supernatant liquids were determined as to fluorescence strength in the same way as given in example 1.

On the other hand, a general cell number of microorganisms contained in each water sample was grown in a standard agar medium at 35° C. for 2 days to count the number of living cells. The relation between fluorescence strength and living cell number thereof is shown in FIG. 1.

Figure 1:
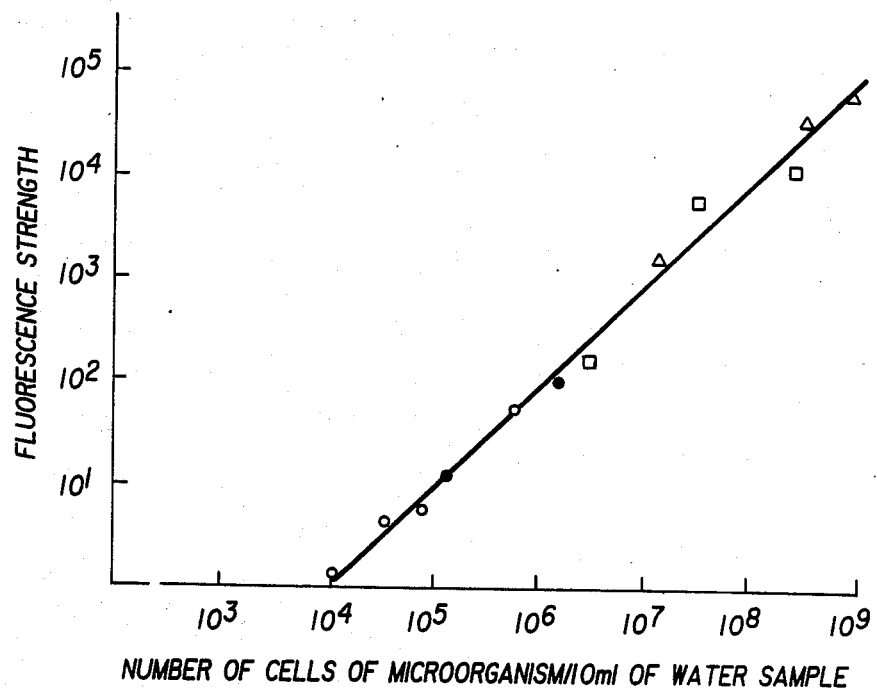
FIG. 1 shows the relation between fluorescence strength and cell number in 10 ml of water sample.

As shown in FIG. 1, it was recognized that there was a correlation between fluorescence strength and living cell number when $10^4$ or more living cells were present in a fixed amount of water sample. Therefore, if $10^4$ or more living cells are present in a water sample, the number of living cells can easily be botained in short time by using the relation shown in FIG. 1 without conducting any cultivation.

EXAMPLE 3

The water of the Tama River was sampled. Into five regular-size test tubes was previously poured 9 ml of HID medium having the composition given in Table 2 and autoclaved at 120° C. for 15 minutes. In the five test tubes thus treated was inoculated each of 1 ml, 0.1 ml, 0.01 ml, and 0.001 ml of the water samples, and the cultures were grown with shaking at 37° C. for 8 hours.

TABLE 2

| HID Medium Composition | |
|---|---|
| Heart infusion (Eiken Co., Ltd.) | 25 g |
| Sodium desoxycholate | 0.5 g |
| Cycloheximide | 100 mg |
| Water | 1000 ml |
| pH | 7.0 |

After the completion of cultivation, the culture solutions were centrifuged at 3500 rpm for 10 minutes (with a H-107 type centrifuge made by Kokusan Centrifuge Co., Ltd.). To each of the resulting precipitate parts was added 2.5 ml of 0.02 M barbital buffer of pH 7.0 containing $10^{-4}$ M of AMC-Leu and $10^{-3}$M of magnesium chloride. The mixtures were treated with a micro ultrasonic wave cell grinder (Sonicator made by Wakenyaku Co. Ltd.) at 50w for 3 minutes. After treatment, these reaction solutions were maintained at 37° C. for 60 minutes. Then, to each of these reaction solutions was added 1 ml of 0.1 M glycine buffer of pH 11.0. After the mixtures were centrifuged at 3000 rpm for 5 minutes, the supernatant liquids were determined as to fluorescence strength in the same way as given in Example 1, and examined to count the number of test tubes of reaction solutions which showed activity for decomposing AMC-Arg to produce AMC.

As to the same water sample, the other cultures were grown at 35° C. for 48 hours according to the BGLB method usually used for the measurement of coliforms to count the number of test tubes which showed the generation of gas during cultivation. The results are given in Table 3.

TABLE 3

| | Comparison Between the Method of This invention and the BGLB Method | |
|---|---|---|
| | Method of measurement | |
| Amount of water sample | The number of water sample test tubes among the five showing positive production of AMC. | The number of BGLB fermentation test tubes showing positive gas generation |
| 1 ml | 5 | 5 |
| 0.1 ml | 5 | 5 |
| 0.01 ml | 3 | 3 |
| 0.001 ml | 0 | 0 |

On the basis of the above results, the number of the living cells contained in a water sample was calculated according to the MPN method to be 79 cells/ml in both methods.

The BGLB method is used for measuring the number of coliforms. Judging from the fact that the number of microorganisms obtained by the method of this inventive Example coincides with that by the BGLB method, it is apparent that the number of coliforms can rapidly be measured by the method of this invention.

EXAMPLE 4

Into regular test tubes was poured 5 ml of each of Heart infusion broth and malt extract - yeast extract broth (0.3% malt extract, 0.3% yeast extract, 2% maltose, 0.1% glucose, pH 6.0), and these media were autoclaved at 120° C. for 10 minutes. In the media of Heart infusion broth were inoculated $10^1$–$10^2$ cells/ml of each of *Escherichia coli* ATCC 25922, *Pseudomonas aeruginosa* ATCC 27853, *Staphylococcus aureus* ATCC 25923, and *Bacillus subtilis* ATCC 1315, and the cultures thereof were grown at 35° C. for 12 hours with shaking. Similarly, in the media of malt extract-yeast extract broth were inoculated $10^2$–$10^3$ cells/ml of each of *Candida albicans* ATCC 10231, *Saccharomyces cerevisiae* CBS 1171, *Aspergillus niger* ATCC 6275, and *Penicillium citrinum* ATCC 9849, and the cultures thereof were grown at 30° C. for 36 hours with shaking.

After the completion of cultivation, these culture solutions were diluted 1000 times with 0.02 M barbital buffer. Then, 1 ml of each of the above diluted solutions was added to each of Solutions A, B, and C shown in Table 4, and each of the mixtures was maintained at 37° C. for 1 hour.

TABLE 4

| Substrate Composition | |
|---|---|
| Substrates contained in 0.02 M barbital buffer of pH 7.0 containing $10^{-4}$ magnesium chloride, and concentrations of the substrates | |
| Solution A | 4MU—P, $10^{-4}$ M + 4MU-Glu, $10^{-4}$ M |
| Solution B | AMC—Arg, $10^{-4}$ M + Boc—Phe—Ser—Arg—AMC*, $10^{-4}$ M |

TABLE 4-continued

Substrate Composition

Substrates contained in 0.02 M barbital buffer of pH 7.0 containing $10^{-4}$ magnesium chloride, and concentrations of the substrates

| Solution C |
|---|
| Solution A + Solution B |

*t-butyl-oxy-carbonyl-phenylalanyl-seryl-arginyl-4-methyl-coumaryl-7-amide.

Next, to each of the reaction solutions was added 1 ml of 1 M glycine buffer at pH 11.0. The resulting mixtures were centrifuged at 3000 rpm for 5 minutes, and the supernatant liquids thereof were measured as to fluorescence strength in the same way as given in Example 1. The results of determining the fluorescence strength of each strain with respect to the three kinds of substrate solutions are shown in Table 5.

TABLE 5

| | Flourescence Strength With Respect to Each Substrate Solution | | |
|---|---|---|---|
| | | Mixed substrate solution | |
| Strain | Solution A | Solution B | Solution C |
| ATCC 25922 | 1800 | 1100 | 4800 |
| ATCC 27853 | 450 | 5500 | 6200 |
| ATCC 25923 | 5500 | 2100 | 6600 |
| ATCC 1315 | 2200 | 300 | 2800 |
| ATCC 10231 | 4200 | 5300 | 8500 |
| CBS 1171 | 6200 | 1100 | 7000 |
| ATCC 6275 | 330 | 4200 | 4800 |
| ATCC 9849 | 280 | 7000 | 7300 |

The numerical figures in Table 5 indicate fluorescence strength.

It was found in all of the strains used that the fluorescence strength was increased when using a mixture of Solutions A and B than when using either Solution A or B alone.

The above fact shows that in the case of some strains having a lower detection sensitivity because the amounts of fluorescence are too small for counting the number of the cells when using Solution A or B alone, Solution C prepared by mixing Solutions A and B should be used for increasing the amount of fluorescence so as to enhance the sensitivity.

EXAMPLE 5

Ten g of each of commercially available potato salad, vegetable salad, and macaroni salad was weighed out under sterile conditions. To each of these samples was added 90 ml of 0.1M phosphoric acid buffer of pH 6.0 containing 0.2% of carboxy methyl cellulose and 0.05% of polysorbate 80, and the mixtures were homogenized with a whirling blender (made by Nippon Seiki Co., Ltd.) at 20,000 rpm for 1 minute. Into each of five regular-size test tubes was previously poured 9 ml of YE medium having the composition given in Table 6, and then the test tubes were autoclaved at 120° C. for 15 minutes. In these five test tubes were inoculated each of 1 ml, 0.1 ml, 0.01 ml, and 0.001 ml of the above homogenized samples, and the cultures were grown at 35° C. for 12 hours with shaking.

TABLE 6

| YE Medium Composition | |
|---|---|
| Yeast extract (Difco product) | 0.3% |
| Peptone (Difco product) | 0.5% |
| Potassium dihydrogen phosphate | 0.05% |
| Glucose | 1.0% |
| pH | 7.0 |

After completion of cultivation, these culture solutions were centrifuged at 3,500 rpm for 10 minutes. To each of the resulting precipitate parts was added 2.5 ml of 0.02M barbitat buffer at pH 7.0 containing $10^{-4}$M of each of AMC-Leu and pyroglutamyl-4-methyl-coumaryl-7-amide (abbreviated as AMC-pyr hereinafter), and the mixtures were maintained at 37° C. for 60 minutes. Then, to each of the reaction solutions was added 1 ml of 0.1M glycine buffer at pH 11.0, and the mixtures were centrifuged at 3,000 rpm for 5 minutes. The above supernatant liquids were measured as to fluorescence strength in the same way as given in Example 1, and the number of the test tubes of reaction solutions having activity for decomposing one or more of the substrates contained in AMC-Leu and AMC-Pyr was counted.

These results are shown in Table 7.

TABLE 7

| | Number of Living Cells in Samples (cells/10 g) | |
|---|---|---|
| Sample | Method of this invention (12 hours) | Standard solution medium method (48 hours) |
| Potato salad | $2.2 \times 10^3$ | $1.7 \times 10^3$ |
| Vegetable salad | $7.9 \times 10^2$ | $7.0 \times 10^2$ |
| Macaroni salad | $8.0 \times 10^1$ | $1.3 \times 10^2$ |

As shown in Table 7, the results of counting the numbers of living cells were in agreement with each other.

EXAMPLE 6

Five samples of 10 ml of the culture solution prepared during the first step of introducing the raw materials for producing sake were taken out. These samples were centrifuged at 3,500 rpm for 10 minutes (with H-107 type centrifuge made by Kokusan Centrifuge Co., Ltd.). To each of the resulting precipitate parts was added 2.5 ml of 0.02 M barbital buffer at pH 7.0 containing $10^{-4}$M of AMC-Leu and $10^{-3}$M of magnesium chloride. The mixtures were treated with a micro ultrasonic wave cell grinder (Sonicator W-10 type made by Wakenyaku Co., Ltd.) at 50w for 3 minutes. After treatment, these reaction solutions were maintained at 37° C. for 60 minutes. After that, to each of the reaction solutions was added 1 ml of 0.1M glycine buffer at pH 11.0, and the mixtures were centrifuged at 3,000 rpm for 5 minutes to measure the resulting supernatant solutions as to fluorescence strength in the same way as given in Example 1.

On the other hand, the yeast contained in each sample was grown in a potato-dextrose agar medium at 25° C. for 5 days to count the number of living cells. The relation between the fluorescence strength and the number ot living cells is shown in FIG. 2.

As clearly shown in FIG. 2, there is a strong correlation between the fluorescence strength and the number of living yeast cells.

EXAMPLE 7

Ten g of each of commercially available rice powder, vegetable salad and frozen gyoza (dumpling stuffed with minced pork) was weighed out under sterile conditions. To each of these samples was added 90 m of 0.1M phosphoric acid buffer at pH 6.0 containing 0.2% of carboxy methyl cellulose and 0.05% of polysorbate 80, and the mixtures were homogenized with a whirling blender (made by Nippon Seiki Co., Ltd.) at 20,000 rpm for 1 minute. Into each of three regularsize test tubes was previously poured 9 ml of YMC medium having the composition given in Table 8, and then the test tubes were autoclaved at 120° C. for 15 minutes. In the three test tubes were inoculated each of 1 ml, 0.1 ml, 0.01 ml, and 0.002 ml of the above homogenized samples, and the cultures were grown at 30° C. for 36 hours with shaking.

AMC-Arg were counted. On the basis of these results, the number of the cells of Eumycetes contained in each sample was calculated according to the Most probable Number method.

As to the same samples, the other cultures were grown at 25° C. for 7 days by using potato dextrose agar media containing 0.01% of chloramphenicol to obtain the number of the cells of Eumycetes by Agar plate Counts method.

These results are shown in Table 9. It is shown in Table 9 that the cell numbers of Eumycetes obtained by the method of this invention are in agreement with

TABLE 9

| Sample name | Amount of sample | Number of test tubes of reaction solution producing fluorescence | Number of colonies by Agar Plate Counts (average of 3 plates) |
|---|---|---|---|
| Rice powder | 0.1 g | 3 | — |
| | 0.01 g | 3 | 9 |
| | 0.001 g | 2 | 1 |
| | 0.0001 g | 0 | 0 |
| | Cell number of Eumycetes calculated by MPN method: 930 cells/g | | Cell number of Eumycetes calculated by colony number: 900 cells/g |
| Vegetable salad | 0.1 g | 3 | — |
| | 0.01 g | 3 | 4 |
| | 0.001 g | 1 | 0.7 |
| | 0.0001 g | 0 | 0 |
| | Cell number of Eumycetes calculated by MPN method: 430 cells/g | | Cell number of Eumycetes calculated by colony number: 400 cells/g |
| Frozen gyoza (dumpling stuffed with minced pork) | 0.1 g | 2 | 0.7 |
| | 0.01 g | 0 | 0 |
| | 0.001 g | 0 | 0 |
| | 0.0001 g | 0 | 0 |
| | Cell number of Eumycetes calculated by MPN method: 9.1 cells/g | | Cell number of Eumycetes calculated by colony number: 7 cells/g |

TABLE 8

| YMC Medium Composition | |
|---|---|
| Yeast extract (Difco product) | 0.2% |
| Peptone (Difco product) | 0.5% |
| Malt extract (Difco product) | 0.3% |
| Maltose | 2.0% |
| Glucose | 0.1% |
| Tween 80 | 0.005% |
| Chloramphenicol | 0.02% |
| pH | 6.0 |

After completion of cultivation, the culture solutions were centrifuged at 3,500 rpm for 10 minutes. To each of the resulting precipitate parts was added 2.5 ml of 0.02M barbital buffer in pH 5.0 containing $10^{-4}M$ of each of 4MU-Gtu, 4MU-P, AMC-Leu and Amc-Acg and $10^{-3}M$ of magnesium chloride, and the resulting mixtures were treated with a micro ultrasonic wave cell grinder (Sonicator W-10 type made by Wakenyaku Col, Ltd.) at 50w for 3 minutes. After treatment, these reaction solutions were maintained at 37° C. for 60 minutes. After that, 1 ml of 0.1M glycine buffer at pH 11.0 was added to each of the reaction solutions. The mixtures were centrifuged at 3,000 rpm for 5 minutes. The resulting supernatant liquids were measured as to fluorescence strength in the same way as given in example 1, and the number of the test tubes of reaction solutions having the activity for decomposing one or more substrates contained in 4MU-P, 4MU-Glu, AMC-Leu, and those by the Agar Plate Counts method with respect to the three kinds of samples.

What is claimed as new and desired to be secured by Letters Patent of the United States is:

1. A method of measuring the number of Eumycete cells in a sample which comprises:
   preparing a solution or suspension containing a sample of a medicine, food, drink, cosmetic or water;
   adding to said solution or suspension an antibiotic capable of inhibiting growth of bacteria but not of Eumycetes;
   maintaining said solution or suspension at 20°–70° C. for 30 minutes to 48 hours;
   adding to said solution or suspension a 7-amino-4-methyl-coumarin derivative represented by formula (1)

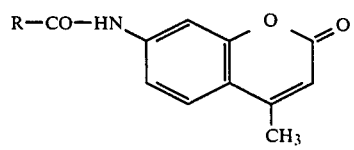

wherein R is an alkyl group, an allyl group, an aralkyl group, or a heterocyclic group, said derivative not inhibiting the hydrolysis of the amide bond of formula (1) by Eumycete hydrolases contained in the sample;

measuring the fluorescence of 7-amino-4-methyl-coumarin released by the Eumycete hydrolases; and ascertaining the number of Eumycete cells based on the relation between fluorescence strength and cell number.

2. A method of measuring the number of Eumycete cells in a sample which comprises:

preparing a solution or suspension containing a sample of a medicine, food, drink, cosmetic or water;

adding to said solution or suspension an antibiotic capable of inhibiting growth of bacteria but not of Eumycetes;

maintaining said solution or suspension at 20°–70° C. for 30 minutes to 48 hours;

adding to said solution or suspension a 7-amino-4-methyl-coumarin derivative represented by formula (1)

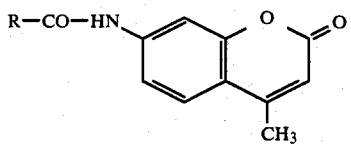

wherein R—CO— in formula (1) represents naturally occurring amino acid residue or a peptide residue, said peptide residue formed from naturally-occurring amino acid residues, said derivative not inhibiting the hydrolysis of the amide bond of formula (1) by Eumycete hydrolases contained in the sample;

measuring the fluorescence of 7-amino-4-methyl-coumarin released by the Eumycete hydrolases; and ascertaining the number of Eumycete cells based on the relation between fluorescence strength and cell number.

3. The method of claim 2 wherein R—CO— in formula (1) represents D or L-leucyl-, or D or L-arginyl- or D or L-pyroglutamyl.

4. The method of claim 2 wherein R—CO— in formula (1) represents Boc-Phe-Ser-Arg-.

5. The method of claim 1 or 2 wherein said antibiotic is pencillin or chloramphenicol.

6. The method of claim 1 or 2 wherein before adding the 7-amino-4-methyl-coumarin derivative to the solution or suspension, said solution or suspension is centrifuged to produce a precipitated material and said precipitated material is used to prepare a second solution and the second solution is used in said method.

7. The method of claim 1, wherein R is a $C_1$–$C_{20}$ alkyl group which may be substituted by one or more functional groups selected from the group consisting of chloro, bromo, fluoro, trifluoromethyl, carboxy, carboxymethyl, and phenyl.

8. The method of claim 7, wherein R is substituted by no more than two of said functional groups.

9. The method of claim 7, wherein R is a $C_1$–$C_5$ alkyl group.

10. The method of claim 1, wherein R is a heterocycle having 5 or 6 ring members where up to 2 of said ring members are heteroatoms.

11. The method of claim 10, wherein said heteroatoms are O, S, or N.

* * * * *